(12) United States Patent
Teisen et al.

(10) Patent No.: US 8,556,949 B2
(45) Date of Patent: Oct. 15, 2013

(54) HYBRID BONE FIXATION ELEMENT AND METHODS OF USING THE SAME

(75) Inventors: Jacques Teisen, Zurich (CH); Simon Stucki, Thun (CH)

(73) Assignee: Depuy Synthes Products, LLC, Raynham, MA (US)

( * ) Notice: Subject to any disclaimer, the term of this patent is extended or adjusted under 35 U.S.C. 154(b) by 964 days.

(21) Appl. No.: 12/270,573

(22) Filed: Nov. 13, 2008

(65) Prior Publication Data

US 2009/0125028 A1 May 14, 2009

Related U.S. Application Data

(60) Provisional application No. 60/987,973, filed on Nov. 14, 2007.

(51) Int. Cl.
*A61B 17/84* (2006.01)
(52) U.S. Cl.
USPC .......................................... 606/327; 606/323
(58) Field of Classification Search
USPC ............. 606/60, 246, 264, 62, 63, 65, 67, 68, 606/286, 300, 301, 304, 309, 310, 313, 326, 606/327, 328, 331, 86 R
See application file for complete search history.

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 4,204,531 A | 5/1980 | Aginsky |
| 4,313,434 A | 2/1982 | Segal |
| 4,655,777 A | 4/1987 | Dunn et al. |
| 4,684,370 A | 8/1987 | Barrett |
| 4,686,973 A | 8/1987 | Frisch |
| 4,733,665 A | 3/1988 | Palmaz |
| 4,735,625 A | 4/1988 | Davidson |
| 4,755,184 A | 7/1988 | Silverberg |
| 4,772,287 A | 9/1988 | Ray et al. |
| 4,854,312 A | 8/1989 | Raftopoulos et al. |
| 4,863,477 A | 9/1989 | Monson |
| 4,888,024 A | 12/1989 | Powder |
| 4,904,260 A | 2/1990 | Ray et al. |
| 4,906,190 A | 3/1990 | Michna |
| 4,932,969 A | 6/1990 | Frey et al. |
| 4,932,975 A | 6/1990 | Main et al. |
| 4,936,848 A | 6/1990 | Bagby |
| 4,969,888 A | 11/1990 | Scholten et al. |
| 4,976,725 A | 12/1990 | Chin et al. |
| 5,015,247 A | 5/1991 | Michelson |
| 5,015,255 A | 5/1991 | Kuslich |

(Continued)

FOREIGN PATENT DOCUMENTS

| | | |
|---|---|---|
| DE | 2558584 | 7/1977 |
| EP | 277282 | 8/1988 |

(Continued)

*Primary Examiner* — Ellen C Hammond
(74) *Attorney, Agent, or Firm* — Meunier Carlin & Curfman, LLC

(57) ABSTRACT

The present invention is directed to a hybrid bone fixation element including a threaded proximal cortical bone contacting portion for threadably engaging the cortical portion of a human bone and a non-threaded expandable distal cancellous portion for engaging the cancellous portion of the human bone. The hybrid bone fixation element can be used, for example, as a pedicle screw, a bone screw or in any other type of bone fixation application.

16 Claims, 6 Drawing Sheets

(56) References Cited

U.S. PATENT DOCUMENTS

| | | | |
|---|---|---|---|
| 5,030,233 A | 7/1991 | Ducheyne | |
| 5,037,445 A | 8/1991 | Santrell | |
| 5,047,055 A | 9/1991 | Bao et al. | |
| 5,053,035 A | 10/1991 | McLaren | |
| 5,059,193 A | 10/1991 | Kuslich | |
| 5,071,435 A | 12/1991 | Fuchs et al. | |
| 5,102,413 A * | 4/1992 | Poddar | 606/62 |
| 5,108,404 A | 4/1992 | Scholten et al. | |
| 5,108,438 A | 4/1992 | Stone | |
| 5,116,305 A | 5/1992 | Milder et al. | |
| 5,133,767 A | 7/1992 | Frey et al. | |
| 5,147,359 A | 9/1992 | Cozad et al. | |
| 5,147,360 A | 9/1992 | Dubousset | |
| 5,154,718 A | 10/1992 | Cozad et al. | |
| 5,171,280 A | 12/1992 | Baumgartner | |
| 5,171,281 A | 12/1992 | Parsons et al. | |
| 5,176,678 A | 1/1993 | Tsou | |
| 5,176,680 A | 1/1993 | Vignaud et al. | |
| 5,176,692 A | 1/1993 | Wilk et al. | |
| 5,190,543 A | 3/1993 | Schlapfer | |
| 5,192,326 A | 3/1993 | Bao et al. | |
| 5,207,678 A | 5/1993 | Harms et al. | |
| 5,209,753 A | 5/1993 | Biedermann et al. | |
| 5,261,907 A | 11/1993 | Vignaud et al. | |
| 5,261,913 A | 11/1993 | Marnay | |
| 5,263,931 A | 11/1993 | Miller | |
| 5,275,600 A | 1/1994 | Allard et al. | |
| 5,275,622 A | 1/1994 | Lazarus et al. | |
| 5,282,801 A | 2/1994 | Sherman | |
| 5,282,863 A | 2/1994 | Burton | |
| 5,303,718 A | 4/1994 | Krajicek | |
| 5,306,307 A | 4/1994 | Senter et al. | |
| 5,306,308 A | 4/1994 | Gross et al. | |
| 5,306,309 A | 4/1994 | Wagner et al. | |
| 5,306,310 A | 4/1994 | Siebels | |
| 5,306,311 A | 4/1994 | Stone et al. | |
| 5,314,477 A | 5/1994 | Marnay | |
| 5,314,478 A | 5/1994 | Oka et al. | |
| 5,331,975 A | 7/1994 | Bonutti | |
| 5,342,298 A | 8/1994 | Michaels et al. | |
| 5,350,379 A | 9/1994 | Spievack | |
| 5,376,123 A | 12/1994 | Klaue et al. | |
| 5,390,683 A | 2/1995 | Pisharodi | |
| 5,437,834 A | 8/1995 | Okimatsu et al. | |
| 5,474,563 A * | 12/1995 | Myler et al. | 606/108 |
| 5,503,164 A | 4/1996 | Friedman | |
| 5,549,679 A | 8/1996 | Kuslich | |
| 5,556,429 A | 9/1996 | Felt | |
| 5,562,704 A | 10/1996 | Tamminmäki et al. | |
| 5,571,189 A | 11/1996 | Kuslich | |
| 5,599,301 A | 2/1997 | Jacobs et al. | |
| 5,601,593 A | 2/1997 | Freitag | |
| 5,626,581 A | 5/1997 | Staehlin et al. | |
| 5,674,295 A | 10/1997 | Ray et al. | |
| 5,707,390 A | 1/1998 | Bonutti | |
| 5,716,416 A | 2/1998 | Lin | |
| 5,749,888 A | 5/1998 | Yock | |
| 5,788,703 A | 8/1998 | Mittelmeier et al. | |
| 5,827,289 A | 10/1998 | Reiley et al. | |
| 5,888,220 A | 3/1999 | Felt et al. | |
| 5,893,850 A | 4/1999 | Cachia | |
| 5,961,554 A | 10/1999 | Janson et al. | |
| 5,972,015 A | 10/1999 | Scribner et al. | |
| 5,989,290 A | 11/1999 | Biedermann et al. | |
| 6,015,436 A | 1/2000 | Schonhoffer | |
| 6,022,376 A | 2/2000 | Assell et al. | |
| 6,025,537 A | 2/2000 | Werding et al. | |
| 6,066,154 A | 5/2000 | Reiley et al. | |
| 6,127,597 A | 10/2000 | Beyar et al. | |
| 6,129,763 A | 10/2000 | Chauvin et al. | |
| 6,149,651 A | 11/2000 | Drewry et al. | |
| 6,174,334 B1 | 1/2001 | Suddaby | |
| 6,176,882 B1 | 1/2001 | Biedermann et al. | |
| 6,183,503 B1 | 2/2001 | Hart et al. | |
| 6,183,518 B1 | 2/2001 | Ross et al. | |
| 6,187,048 B1 | 2/2001 | Milner et al. | |
| 6,213,775 B1 | 4/2001 | Reipur | |
| 6,224,630 B1 | 5/2001 | Bao et al. | |
| 6,241,734 B1 | 6/2001 | Scribner et al. | |
| 6,245,107 B1 | 6/2001 | Ferree | |
| 6,248,110 B1 | 6/2001 | Reiley et al. | |
| 6,248,131 B1 | 6/2001 | Felt et al. | |
| 6,261,289 B1 | 7/2001 | Levi | |
| 6,306,177 B1 | 10/2001 | Felt et al. | |
| 6,319,255 B1 | 11/2001 | Grundei et al. | |
| 6,383,190 B1 | 5/2002 | Preissman | |
| 6,395,032 B1 | 5/2002 | Gauchet | |
| 6,425,923 B1 | 7/2002 | Stalcup et al. | |
| 6,428,576 B1 | 8/2002 | Haldimann | |
| 6,443,988 B2 | 9/2002 | Felt et al. | |
| 6,478,800 B1 | 11/2002 | Fraser et al. | |
| 6,482,235 B1 | 11/2002 | Lambrecht et al. | |
| 6,508,839 B1 | 1/2003 | Lambrecht et al. | |
| 6,554,833 B2 | 4/2003 | Levy et al. | |
| 6,582,471 B1 | 6/2003 | Bittmann et al. | |
| 6,592,625 B2 | 7/2003 | Cauthen | |
| 6,852,095 B1 | 2/2005 | Ray | |
| 6,869,445 B1 | 3/2005 | Johnson | |
| 7,153,306 B2 * | 12/2006 | Ralph et al. | 606/92 |
| 7,547,324 B2 * | 6/2009 | Cragg et al. | 623/17.11 |
| 2001/0000186 A1 | 4/2001 | Bramlet et al. | |
| 2002/0045942 A1 | 4/2002 | Ham | |
| 2002/0068939 A1 | 6/2002 | Levy et al. | |
| 2002/0068974 A1 | 6/2002 | Kuslich et al. | |
| 2002/0156531 A1 | 10/2002 | Felt et al. | |
| 2003/0033017 A1 | 2/2003 | Lotz et al. | |
| 2003/0088249 A1 | 5/2003 | Furderer | |
| 2003/0220649 A1 | 11/2003 | Bao et al. | |
| 2004/0073308 A1 | 4/2004 | Kuslich et al. | |
| 2004/0097930 A1 | 5/2004 | Justis et al. | |
| 2004/0122431 A1 * | 6/2004 | Biedermann et al. | 606/73 |
| 2005/0113929 A1 * | 5/2005 | Cragg et al. | 623/17.16 |
| 2005/0187555 A1 | 8/2005 | Biedermann et al. | |
| 2005/0234498 A1 | 10/2005 | Gronemeyer et al. | |
| 2006/0100706 A1 | 5/2006 | Shadduck et al. | |
| 2007/0093899 A1 * | 4/2007 | Dutoit et al. | 623/17.11 |
| 2007/0198018 A1 | 8/2007 | Biedermann et al. | |
| 2008/0288003 A1 * | 11/2008 | McKinley | 606/313 |
| 2009/0131992 A1 * | 5/2009 | Greenhalgh et al. | 606/313 |
| 2010/0016905 A1 * | 1/2010 | Greenhalgh et al. | 606/313 |

FOREIGN PATENT DOCUMENTS

| | | |
|---|---|---|
| EP | 321020 | 6/1989 |
| EP | 0322334 | 6/1989 |
| EP | 0480954 | 4/1992 |
| EP | 0854198 | 7/1998 |
| FR | 2603256 | 3/1988 |
| FR | FR2629337 | 10/1989 |
| FR | 2639823 | 6/1990 |
| FR | 2662073 | 11/1991 |
| FR | 2707477 | 1/1995 |
| FR | 2708192 | 2/1995 |
| FR | 2712486 | 5/1995 |
| FR | 2714590 | 7/1995 |
| FR | 2718634 | 10/1995 |
| FR | 2722679 | 1/1996 |
| FR | 2725892 | 4/1996 |
| FR | 2727304 | 5/1996 |
| FR | 2753080 | 3/1998 |
| FR | 2778082 | 11/1999 |
| FR | 2 787 313 | 6/2000 |
| FR | 2787313 | 6/2000 |
| FR | 2791551 | 10/2000 |
| FR | 2794019 | 12/2000 |
| FR | 2796846 | 2/2001 |
| FR | 2799117 | 4/2001 |
| FR | 2803532 | 7/2001 |
| GB | 2114005 | 8/1983 |
| RU | 2033755 | 4/1995 |
| RU | 2056797 | 3/1996 |
| RU | 2178681 | 1/2002 |
| SU | 906530 | 2/1982 |
| SU | 995751 | 2/1983 |

(56) References Cited

FOREIGN PATENT DOCUMENTS

| | | |
|---|---|---|
| SU | 1811865 | 4/1993 |
| WO | WO91/00713 | 1/1991 |
| WO | WO93/16664 | 9/1993 |
| WO | WO9420166 | 9/1994 |
| WO | WO9421320 | 9/1994 |
| WO | WO 98/56301 | 12/1998 |
| WO | WO9856301 | 12/1998 |
| WO | WO9902108 | 1/1999 |
| WO | WO99/26554 | 6/1999 |
| WO | WO00/44319 | 8/2000 |
| WO | 2164152 | 3/2001 |
| WO | WO01/21246 | 3/2001 |
| WO | WO0128464 | 4/2001 |
| WO | WO 01/54598 | 8/2001 |
| WO | WO 01/76514 | 10/2001 |
| WO | WO0176514 | 10/2001 |
| WO | WO 02/43628 | 6/2002 |
| WO | WO02/43628 | 6/2002 |
| WO | WO 03/007853 | 1/2003 |
| WO | WO2005/048856 | 6/2005 |
| WO | WO 2006/068682 | 6/2006 |
| WO | WO 2006/116760 | 11/2006 |
| WO | WO2006124764 | 11/2006 |
| WO | WO 2008/112308 | 9/2008 |

* cited by examiner

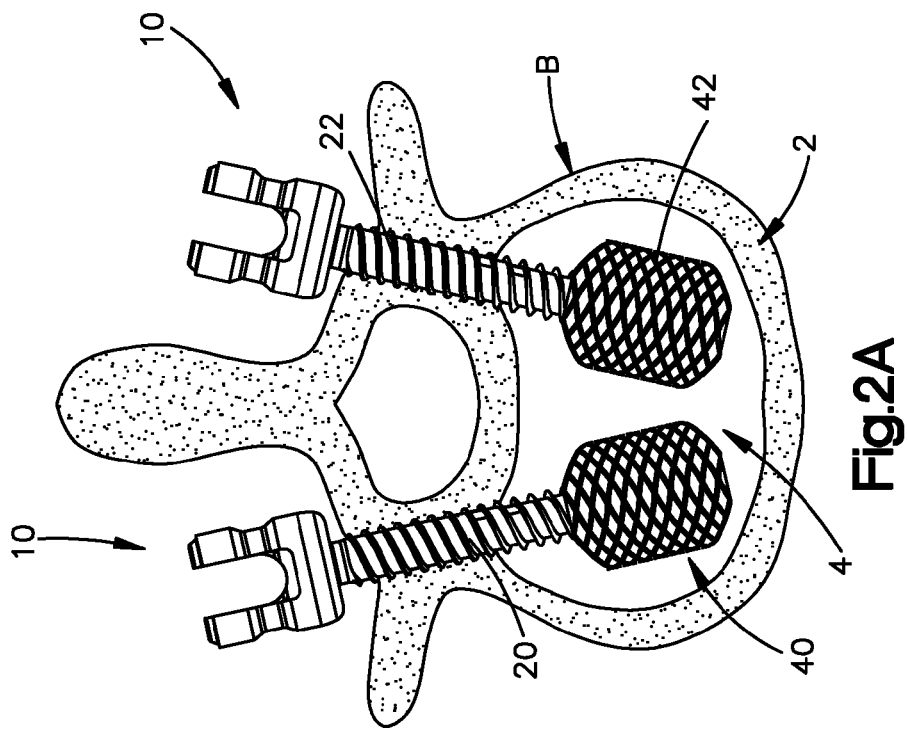
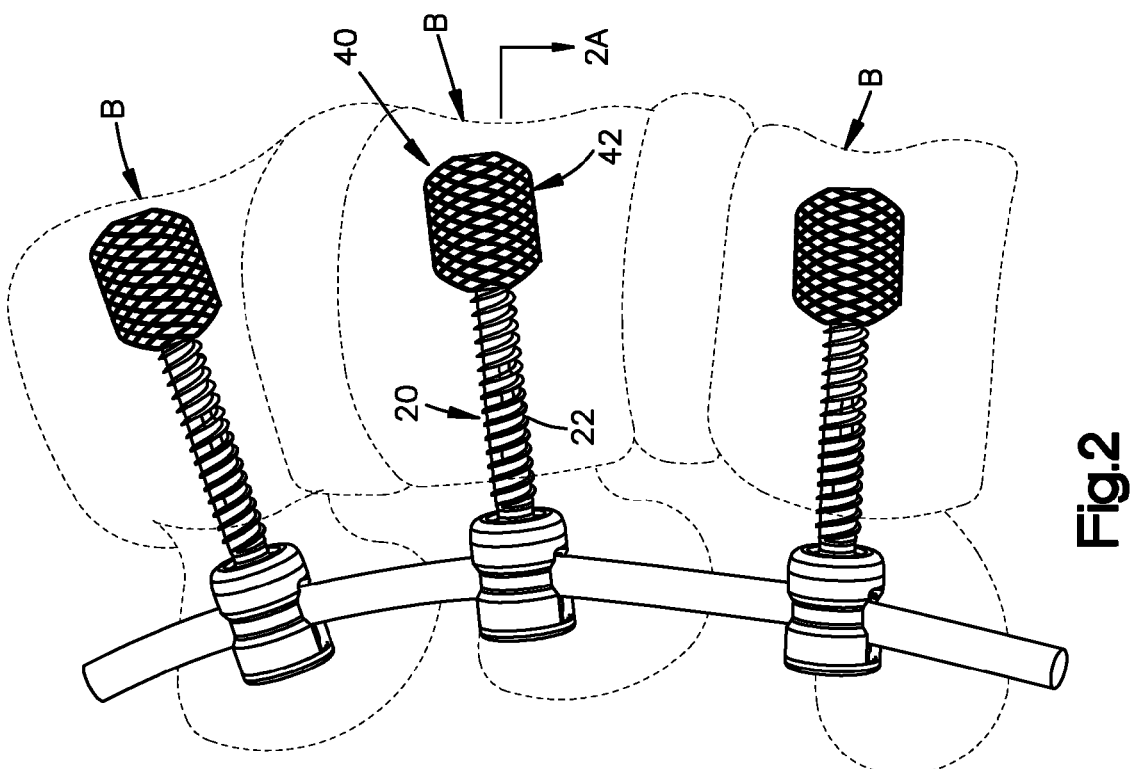

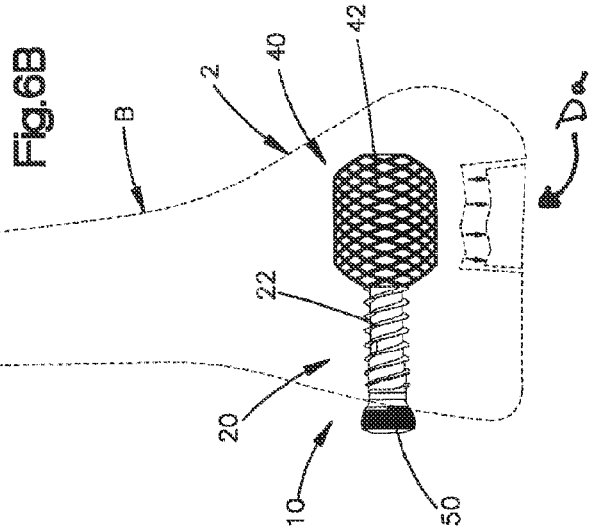
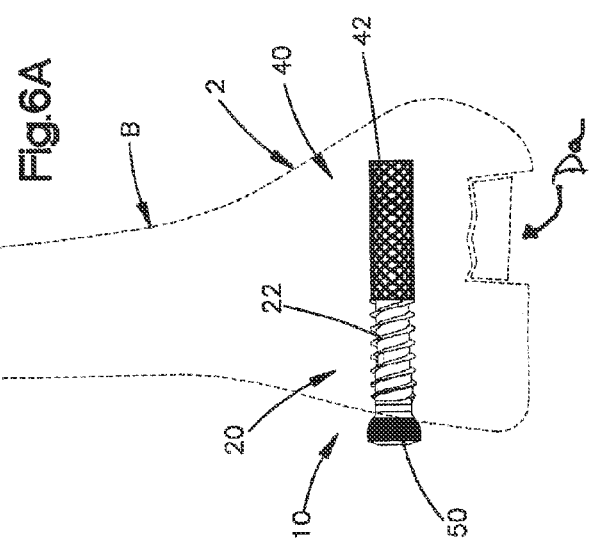

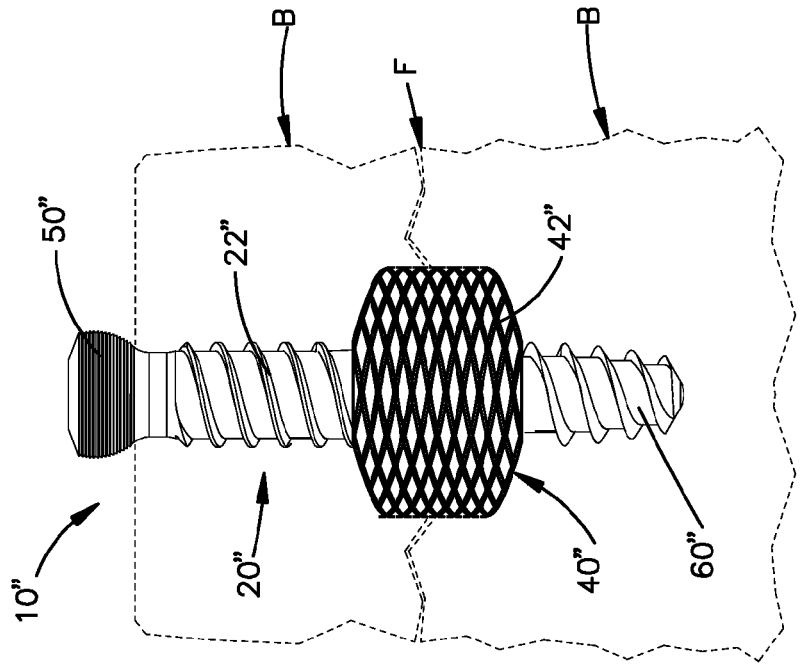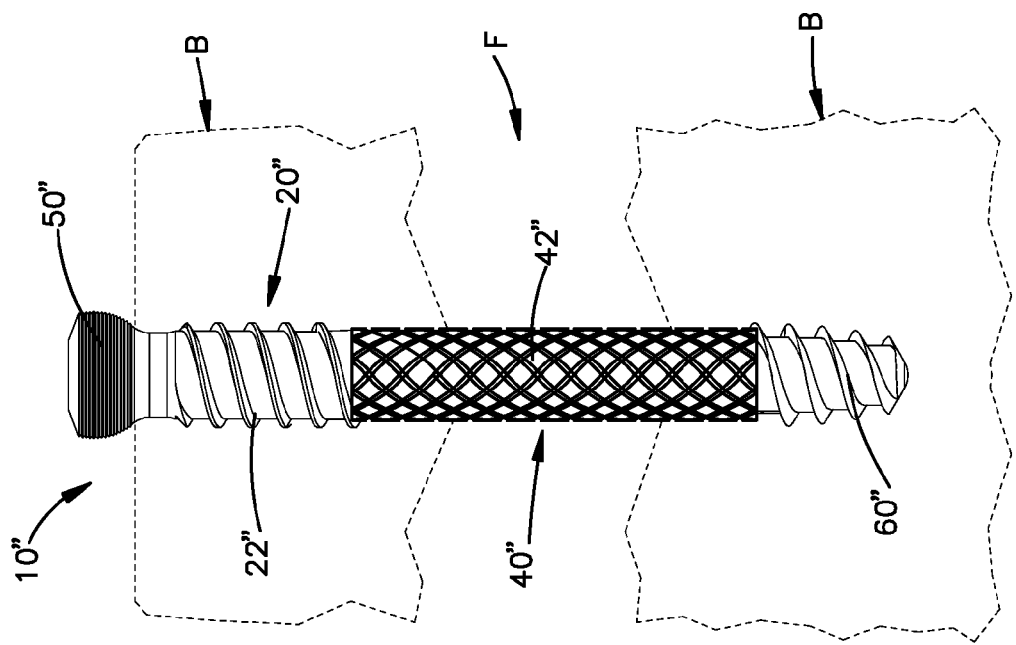

HYBRID BONE FIXATION ELEMENT AND METHODS OF USING THE SAME

CROSS-REFERENCE TO RELATED APPLICATIONS

This application claims the benefit of U.S. Provisional Application No. 60/987,973, filed on Nov. 14, 2007, titled "Hybrid Bone Screw," the contents of which is hereby incorporated by reference in its entirety.

BACKGROUND OF THE INVENTION

Generally speaking, human bone is formed by a hard, thinner cortical outer portion surrounding a softer cancellous inner portion. Conventional bone screws include a threaded shaft for engaging and obtaining purchase in the bone. The bone screw may be manually inserted into the bone by, for example, a screw driver. In use, torque is applied to the bone screw to drive or rotate the screw so that it is inserted into the cortical and cancellous portions of the bone. However, generally speaking, substantially all, if not all, of the bone screw's purchase is achieved via the engagement of the threads with the cortical outer portion. That is, the interaction between the threads and the cancellous inner portion of the human bone add little, if any, purchase as the cancellous inner portion is too soft for threadably engaging the threads of the bone screw.

Thus there exists a need for a new and improved bone fixation element that will take into account the different properties of the human bone in order to increase the purchase strength between the human bone and the bone fixation element.

BRIEF SUMMARY OF THE INVENTION

The present invention is directed to an improved bone fixation element and method of using the same. More specifically, the present invention is directed to a hybrid bone fixation element including a proximal cortical bone contacting portion for contacting and/or engaging the cortical outer portion of a human bone and an expandable distal cancellous portion for contacting and/or engaging the cancellous inner portion of the human bone. The hybrid bone fixation element can be used, for example, as a pedicle screw, a bone screw or in any other type of bone fixation application.

In one preferred embodiment, the hybrid bone fixation element includes a threaded proximal cortical bone contacting portion for threadably engaging a cortical outer portion of a patient's bone and a non-threaded expandable distal cancellous bone contacting portion for engaging a cancellous inner portion of the patient's bone. The non-threaded expandable distal cancellous bone contacting portion is preferably an expandable stent coupled to the threaded proximal cortical bone contacting portion. The expandable stent is preferably expanded from a first insertion configuration to a second expanded configuration via a balloon-catheter inserted into the expandable distal cancellous bone contacting portion via a cannulated bore formed therein. The first insertion position preferably has a first radial diameter and the second expanded configuration preferably has a second radial diameter, the second radial diameter being larger than the first radial diameter. The hybrid bone fixation element may also include an enlarged head portion coupled to the threaded proximal cortical bone contacting portion.

In use, the hybrid bone fixation element is preferably inserted into a patient's bone by forming an insertion hole in the cortical outer portion of the patient's bone. Next at least a portion of the non-threaded. expandable distal cancellous bone contacting portion is inserted through the insertion hole formed in the cortical outer portion of the patient's bone and into the cancellous inner portion of the patient's bone. Once the threaded proximal cortical bone contacting portion contacts the cortical outer portion of the patient's bone, the hybrid bone fixation element is threaded so that the threaded proximal cortical hone contacting portion threadably engages the cortical outer portion. Once the hybrid bone fixation element is properly placed, an expandable balloon is inserted into the cannulated bore formed in the hybrid bone fixation element so that the non-threaded expandable distal cancellous bone contacting portion is expanded within the cancellous inner portion of the patient's bone via the expandable balloon.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the hybrid bone fixation element of the present application, there is shown in the drawings preferred embodiments. It should be understood, however, that the application is not limited to the precise arrangements and instrumentalities shown. In the drawings:

FIG. 2 is a perspective view of the exemplary hybrid bone fixation element being used in a pedicle screw fixation system in accordance with one aspect of the present invention;

FIG. 2A is a cross-sectional view of the hybrid bone fixation element taken along line 2A-2A shown in FIG. 2;

FIG. 6A is a side view of a patient's bone having a depressed area;

FIG. 6B is a side view of an exemplary embodiment of a hybrid bone fixation element implanted within the patient's bone to substantially fix the depressed area;

FIG. 7A is a side view of an alternate exemplary embodiment of a hybrid bone fixation element implanted within a patient's bone across a fracture site; and FIG. 7B is a side view of the hybrid bone fixation element shown in FIG. 7A in the expanded configuration to reduce the fracture in accordance with another aspect of the present invention.

DETAILED DESCRIPTION OF THE INVENTION

Figure 1A:
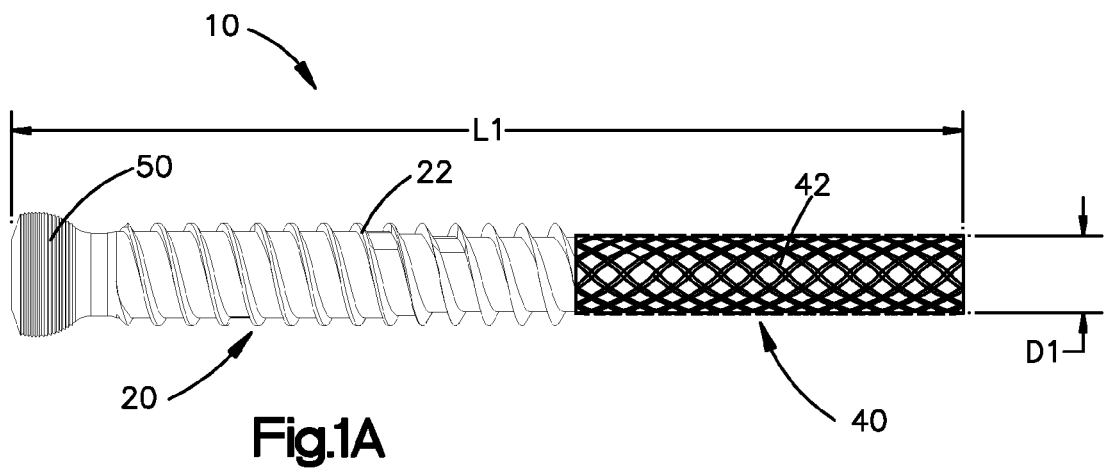
FIG. 1A is a side view of an exemplary embodiment of a hybrid bone fixation element in accordance with one aspect of the present invention, the hybrid bone fixation element is illustrated in an insertion configuration.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to a hybrid bone fixation element 10 for engaging a human bone B. The hybrid bone fixation element 10 preferably includes a first cortical bone contacting portion 20 and a second cancellous bone contacting portion 40. As will be described in greater detail below, preferably the first cortical bone contacting portion 20 is a proximal cortical bone contacting portion 20 and includes a threaded shaft portion 22 for threadably engaging the cortical outer portion 2 of the human bone B. The second cancellous bone contacting portion 40 preferably is a distal expandable cancellous bone contacting portion 40 and is in the form of an expandable stent 42 for contacting and/or engaging the cancellous inner portion 4 of the human bone B. The hybrid bone fixation element 10 may also include an enlarged head portion 50 and preferably includes a longitudinal bore 21 extending therethrough. The bore 21 may extend through both ends of the hybrid bone fixation element 10 or only extend partially along its length. As will be appreciated by one of ordinary skill in the art, the first cortical bone contacting portion 20 may be non-threaded and/or the second cancellous bone contacting portion 40 may be threaded. Alternatively and/or in addition, the first cortical bone contacting portion 20 may be distal and the second cancellous bone contacting portion 40 may be proximal depending on the procedure being performed.

In use, an insertion hole may be formed in the bone B, the hole being sized and configured to receive at least a portion of the hybrid bone fixation element 10 so that the expandable distal cancellous bone contacting portion 40 can be inserted through the cortical outer portion 2 of the bone B and into the cancellous inner portion 4 until the threaded proximal cortical bone contacting portion 20 contacts the cortical outer portion 2 of the bone B. Next the surgeon rotates the hybrid bone fixation element 10 via, for example, a screw driver, so that the threaded proximal cortical bone contacting portion 20 threadably engages the cortical outer portion 2. Once the hybrid bone fixation element 10 has achieved its desired location, the surgeon preferably expands the expandable distal cancellous bone contacting portion 40 to increase the purchase strength of the hybrid bone fixation element 10 with respect to the bone B.

Figure 1B:
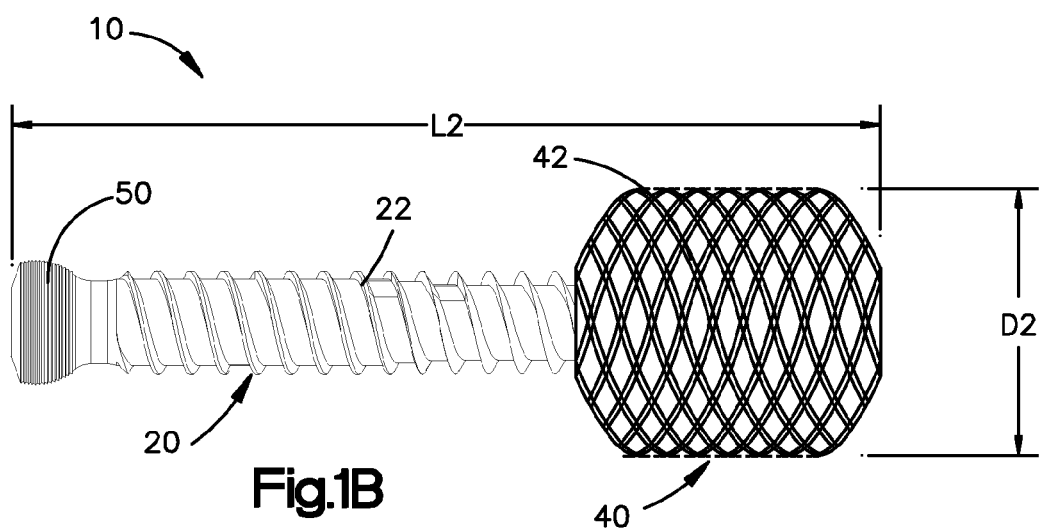
FIG. 1B is a side view of the hybrid bone fixation element shown in FIG. 1A in an expanded configuration.
Figures 1C, 1D:
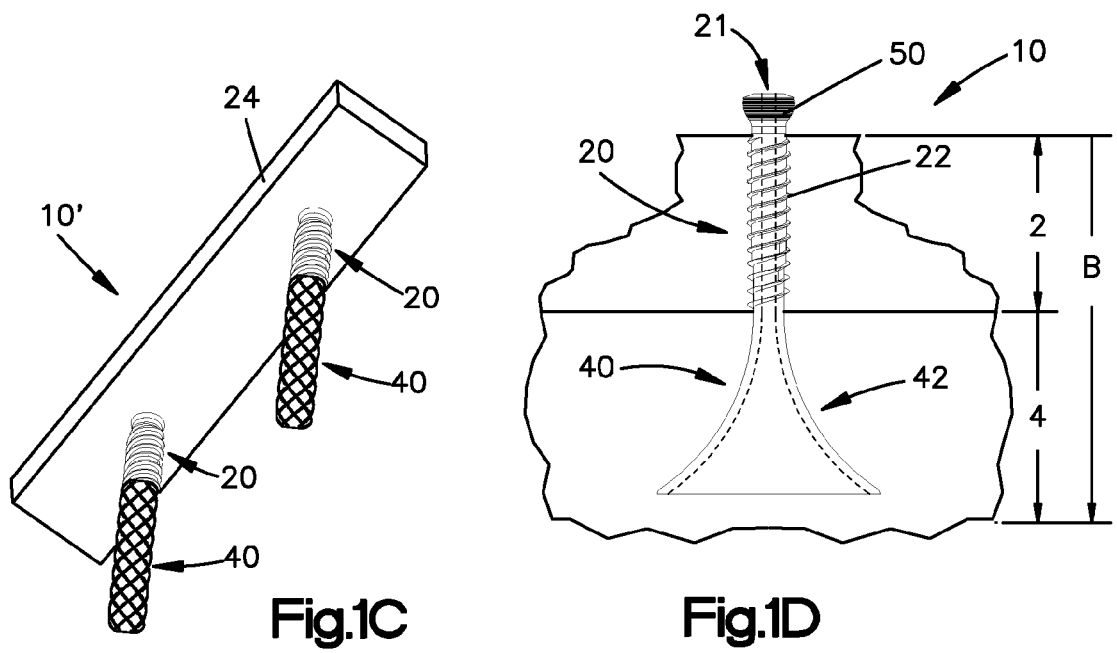
FIG. 1C is a bottom perspective view of an alternate exemplary embodiment of a hybrid bone fixation element in accordance with another aspect of the present invention.
FIG. 1D is a side view of an alternate exemplary embodiment of a hybrid bone fixation element implanted within a patient's bone, the hybrid bone fixation element illustrated in the expanded configuration.

Referring generally to FIGS. 1A and 1B, the present invention is generally directed to a hybrid bone fixation element 10 and to a method for inserting the hybrid bone fixation element 10 into a targeted human bone B. The hybrid bone fixation element 10 includes a proximal cortical bone contacting portion 20 and an expandable distal cancellous bone contacting portion 40. The hybrid bone fixation element 10 preferably includes a cannulated bore 21 (as best shown in FIG. 1D) for reasons that will become apparent below.

Preferably, the proximal cortical bone contacting portion 20 is in the form of an externally threaded shaft 22 for threadably engaging the cortical outer portion 2 of the human bone B (as best shown in FIG. 2A). The specific features of the externally threaded shaft 22 including, for example, thread pitch, shaft diameter, shaft shape, etc. are interchangeable, and it would be apparent to one having ordinary skill in the art that the proximal threaded cortical bone contacting portion 20 is not limited to any particular type of thread. Alternatively, as best shown in FIG. 1C, the hybrid bone fixation element 10' may include, for example, a proximal cortical bone contacting portion 20 including an integrally coupled plate 24 having one or more expandable distal cancellous bone contacting portions 40 extending therefrom.

Figure 4:
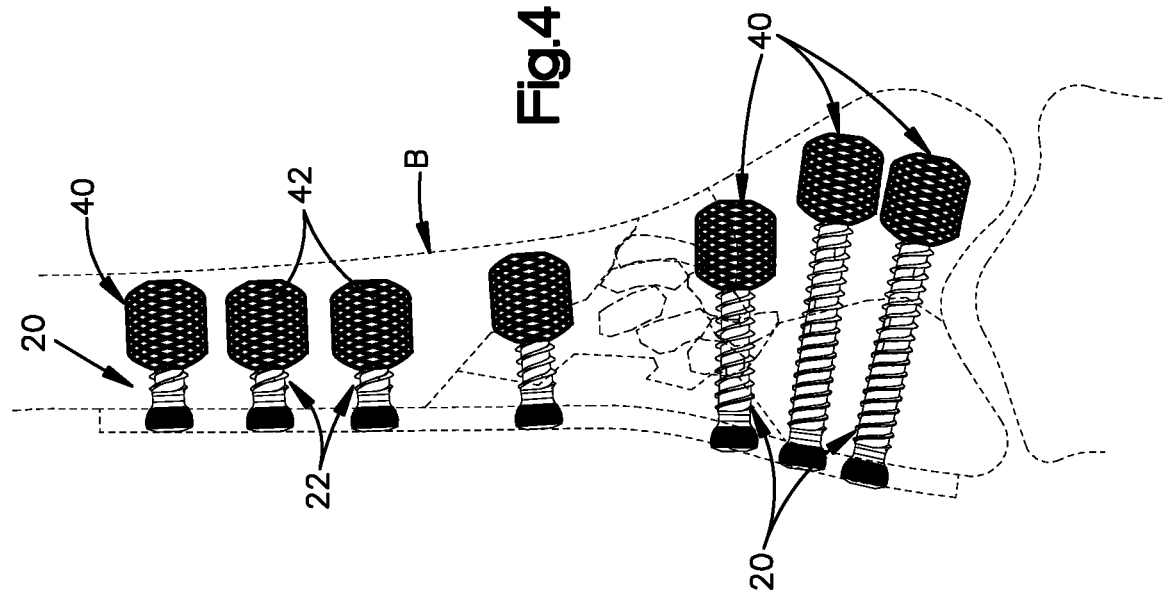
FIG. 4 is a perspective view of the exemplary hybrid bone fixation element being used in connection with a plate in accordance with one aspect of the present invention.
Figure 5:
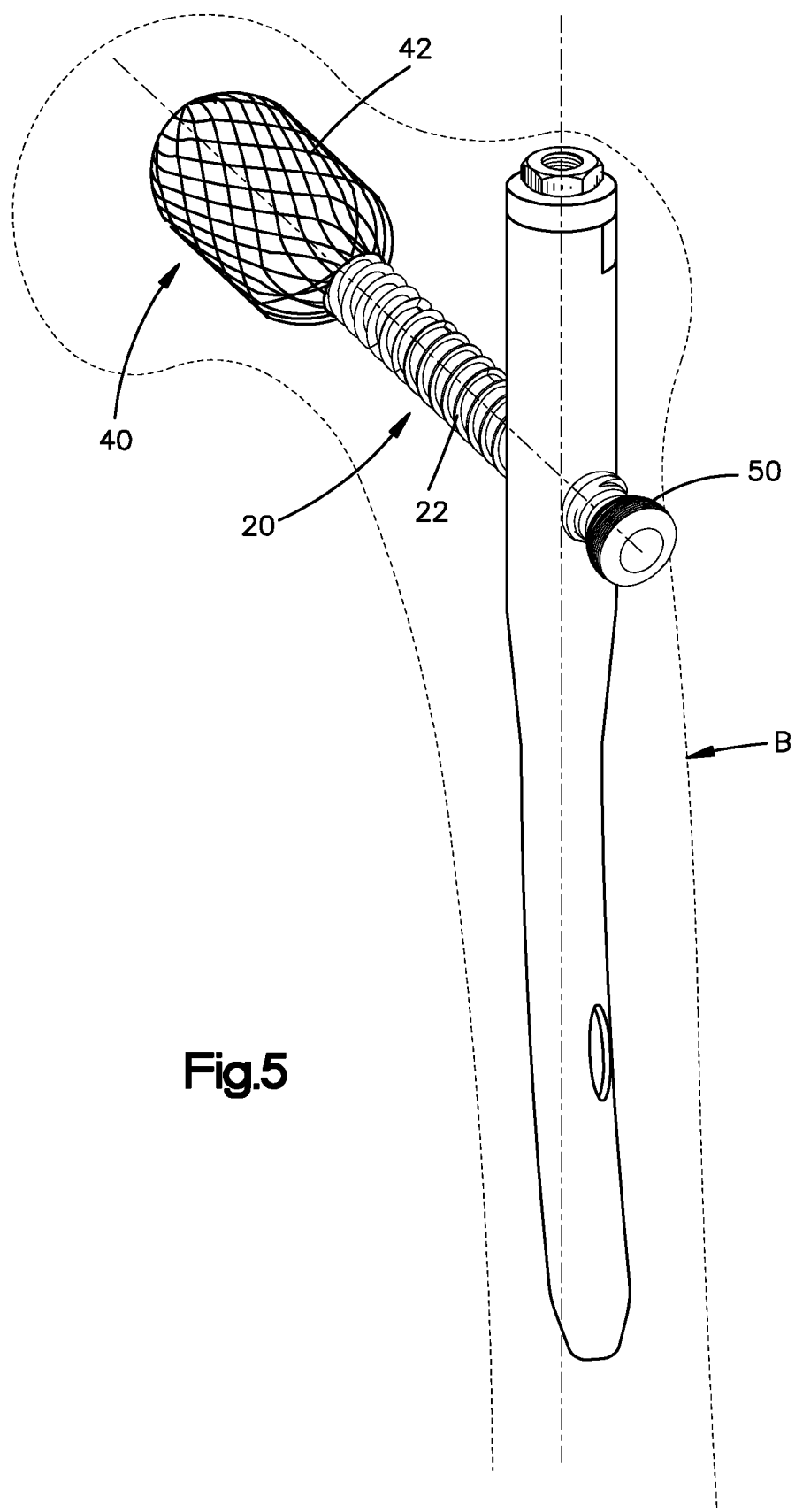
FIG. 5 is a perspective view of the exemplary hybrid bone fixation element being used in connection with a femur fixation procedure in accordance with one aspect of the present invention.

The expandable distal cancellous bone contacting portion 40 is preferably in the form of an expandable stent 42. The expandable distal cancellous bone contacting portion 40 may be in the form of an expandable stent 42 wherein the entire distal portion of the hybrid bone fixation element 10 is expandable from a first insertion configuration (as generally shown in FIG. 1A) to a second expanded configuration (as generally shown in FIG. 1B). In the second expanded configuration, the expandable distal cancellous bone contacting portion 40 may have any shape now or hereafter known in the art including, for example, barrel, dumbbell, disc, cylindrical, etc. Preferably, in the second expanded configuration, the expandable distal cancellous bone contacting portion 40 has a bulbous shape (as best shown in FIGS. 1B, 2, 2A, 3, 4,5, 6B and 7B) or a funnel shape (as best shown in FIG. 1D) so that the outer diameter of the expandable stent 42 is maximized. As shown in FIG. 5, for example, the stent 42 may be comprised of a plurality of intersecting helices with opposite orientation. The intersecting helices define between them a plurality of holes. For example, the intersecting helices of the stent 42 in FIG. 5 form diamond-shaped holes wherein each of the holes has a closed periphery.

Moreover, in the first insertion configuration, the expandable distal cancellous bone contacting portion 40 preferably has a first radial diameter D1. The hybrid bone fixation element 10, in the first insertion configuration, preferably has a first overall length L1. In the second expanded configuration, the expandable distal cancellous bone contacting portion 40 preferably has a second radial diameter D2. The hybrid bone fixation element 10, in the second expanded configuration, preferably has a second overall length L2. The second radial diameter D2 preferably is larger than the first radial diameter D1 while the second overall length L2 is preferably shorter than the first overall length L1. Thus expansion of the expandable distal cancellous bone contacting portion 40 preferably causes the length of the hybrid bone fixation element 10 to shorten while causing the diameter of the expandable distal cancellous bone contacting portion 40 to expand.

The expandable distal cancellous bone contacting portion 40 may alternatively be in the form of a deformable portion wherein deformation of the expandable distal portion causes the expandable distal cancellous bone contacting portion 40 to expand.

The expandable distal cancellous bone contacting portion 40 may be coupled to the proximal cortical bone contacting portion 20 by any means now or hereafter known in the art including, but not limited to, a mechanical connection, threads, welding, bonding, press-fit connection, etc. Alternatively, the expandable distal cancellous bone contacting portion 40 may be integrally formed with the proximal cortical bone contacting portion 20.

The expandable distal cancellous bone contacting portion 40 may be expanded by any means now or hereafter known in the art. For example, in the preferred embodiment wherein the expandable distal cancellous bone contacting portion 40 is an expandable stent 42, the expandable distal cancellous bone contacting portion 40 may be expanded by a balloon-catheter inserted into the expandable distal cancellous bone contacting portion 40 via the cannulated bore 21 formed in the hybrid bone fixation element 10. The inflatable balloon, and hence the expandable distal cancellous bone contacting portion 40, may be expanded by injection of a contrast liquid via a high pressure inflation syringe connected to the balloon-catheter. Alternatively, the balloon may be expanded by injection of, for example, a cement. Once the cement cures, the expandable distal cancellous bone contacting portion 40 is maintained in the expanded configuration by the cured cement. Moreover, the balloon may be expanded by injection of a gas or by way of a chemical reaction. Moreover, any other means for expanding the expandable distal cancellous bone contacting portion 40 may be used including, for example, the direct injection of cement into the expandable distal cancellous bone contacting portion 40 without the incorporation of a balloon, a surgical instrument or tool, etc.

The hybrid bone fixation element 10 may also include an enlarged head portion 50. The head portion 50 preferably includes a drive surface (not shown) for receiving a corresponding tip formed on a drive tool, such as a screw driver (not shown) for rotating the hybrid bone fixation element 10 into engagement with the bone. The drive surface may have any form now or hereafter known including, but not limited to, an internal recess for engaging a corresponding external drive feature, an external hexagon, a star drive pattern, a Phillips head pattern, a slot for a screw driver, a threading for a correspondingly threaded post, etc.

Figure 3:
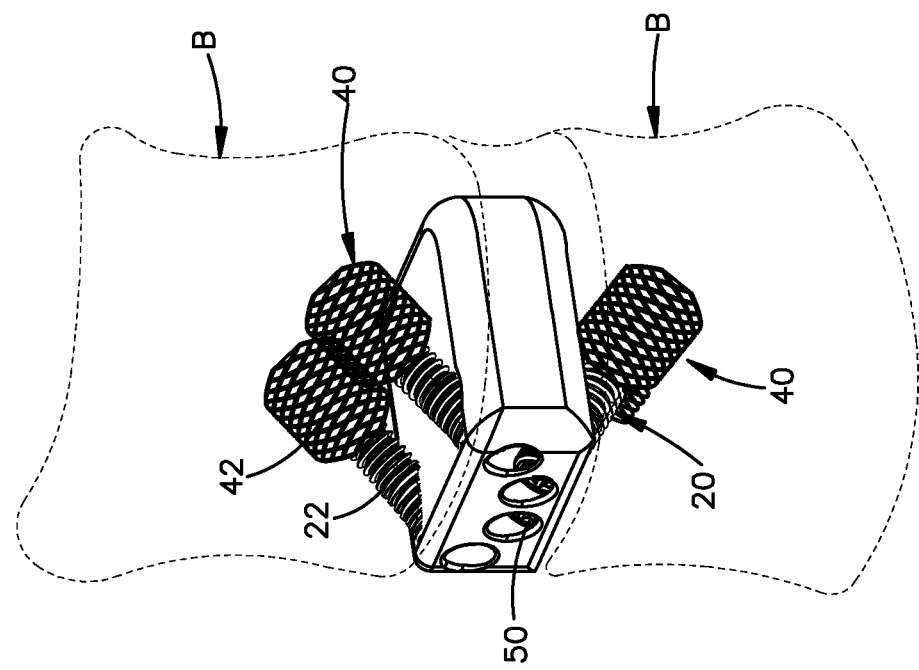
FIG. 3 is a perspective view of the exemplary hybrid bone fixation element being used in connection with an intervertebral implant in accordance with one aspect of the present invention.

In use, the hybrid bone fixation element 10 can be used, for example, as a bone fixation element in a pedicle screw system (as best shown in FIG. 2) in connection with a spinal fusion procedure. Alternatively, the hybrid bone fixation element 10 can be used, for example, as a bone fixation element in connection with the securement of a vertebral implant (as best shown in FIG. 3). Moreover, the hybrid bone fixation element 10 can be used, for example, as a bone fixation element for securing a bone plate to a patient's bone such as, for example, in connection with a fixation of a long bone (as best shown in FIG. 4) or adjacent vertebral bodies. Furthermore, the hybrid bone fixation element 10 can be used, for example, as a bone fixation element in a femur fixation procedure (as best shown in FIG. 5). Alternatively, the hybrid bone fixation element 10 can be used in any other type of bone fixation application either now or hereafter known such as, for example, in connection with a proximal tibia fixation procedure, a proximal humerus fixation procedure, etc.

In addition, as best shown in FIGS. 6A and 6B, the hybrid bone fixation element 10 can be used as a stand alone device to, for example, move a portion of the cortical outer portion 2 of the patient's bone B. That is, for example, in a pilon fracture, the patient's cortical outer portion 2 may move or collapse thereby forming a depressed area Da. The hybrid bone fixation element 10 can be used to move and subsequently reinforce the cortical outer portion 2 of the patient's bone B in order to return the cortical outer portion 2 substantially to its original condition. Reduction of the depressed area Da may be achieved by inserting the hybrid bone fixation element 10 into the bone B adjacent to the depressed area Da. Thereafter subsequent expansion of the expandable distal cancellous bone contacting portion 40 may cause the cortical outer portion 2 of the patient's bone B to move to its original, non depressed condition.

Furthermore, the hybrid bone fixation element 10" may be used as a stand alone device in, for example, a fracture reduction procedure. That is, as best shown in FIGS. 7A and 7B, the hybrid bone fixation element 10" may include a threaded proximal portion 22", a threaded distal portion 60" and an expandable central portion 40". In use, the hybrid bone fixation element 10" is inserted in the bone B so that the expandable central portion 40" spans the bone fracture F. Thereafter, subsequent expansion of the expandable central portion 40" causes the overall length of the hybrid bone fixation element 10" to shorten thus reducing or closing the fracture F. Preferably, the hybrid bone fixation element 10" permits a shortening distance of about 5% to about 40%.

An exemplary method of inserting the hybrid bone fixation element 10 will now be described. As will be generally appreciated by one of ordinary skill in the art, the hybrid bone fixation element 10 may be used in connection with this or other surgical methods. With the patient in a prone position, an X-ray is preferably taken to assist in confirming the precise patient positioning for surgery. Depending on the particular surgical procedure being performed, access can be either via a minimally invasive surgical system such as, for example, a cannula or via an open surgical incision. Once the desired surgical site is identified, a guide wire, trocar or other similar device may be used to assist the surgeon in guiding the hybrid bone fixation elements 10 and/or various surgical instruments into place. An insertion hole is then formed in the cortical outer portion 2 of the bone B in the desired locations. If necessary, depending on the particular surgical procedure being performed, an implant such as, for example, an intervertebral implant, a bone plate, etc. is implanted. Next, the hybrid bone fixation elements 10 are inserted through the implant, if necessary, and into contact with the bone B. Preferably, the hybrid bone fixation element 10, and more preferably, the expandable distal cancellous bone contacting portion 40 is inserted through the cortical outer portion 2 of the bone B and into the cancellous inner portion 4 until the proximal cortical bone contacting portion 20 contacts the cortical outer portion 2 of the bone B. The surgeon rotates the hybrid bone fixation element 10 via, for example, a screw driver, so that the threaded proximal cortical bone contacting portion 20 threadably engages the cortical outer portion 2. Once the hybrid bone fixation element 10 has achieved its desired location, the surgeon preferably expands the expandable distal cancellous bone contacting portion 40 to increase the purchase strength of the hybrid bone fixation element 10 with respect to the bone B.

The expandable distal cancellous bone contacting portion 40 may be expanded by inserting a balloon-catheter into the expandable distal cancellous bone contacting portion 40 via the cannulated bore 21. Thereafter inflation of the balloon-catheter gradually expands the expandable distal cancellous bone contacting portion 40. Once the expandable distal cancellous bone contacting portion 40 is properly expanded, the balloon-catheter is deflated and removed. Optionally, a bone cement may be inserted through the cannulated bore 21 to further solidify the expandable distal cancellous bone contacting portion 40 to the cancellous inner portion 4.

The expandable distal cancellous bone contacting portion 40 may include one or more projections (not shown) formed thereon for increasing the purchase between the expandable distal cancellous bone contacting portion 40 and the cancellous inner portion 4. The projections may be in the form, for example, of teeth, ridges, undulations, etc. Alternatively and/or in addition, the expandable distal cancellous bone contacting portion 40 may be coated with a chemical additive.

The expandable distal cancellous bone contacting portion 40 may also be sized and configured to be longitudinally expandable or telescopic. In this manner, for example, the expandable distal cancellous bone contacting portion 40 may reside inside of the proximal cortical bone contacting portion 20. This may help to protect the expandable distal cancellous bone contacting portion 40 during insertion and may also eliminate the need for pre-drilling an insertion hole. For example, in use, the proximal cortical bone contacting portion 20 may be inserted into the bone B, either with or without a pre-drill insertion hole. Thereafter, the inflatable balloon and fluid may be inserted into the hybrid bone fixation element 10 causing the expandable distal cancellous bone contacting portion 40 to telescope longitudinally out of the proximal bone contacting portion 20. Additional insertion of fluid may also cause the expandable distal cancellous bone contacting portion 40 to expand in the transverse direction. Alternatively, the expandable distal cancellous bone contacting portion 40 may be longitudinally expandable without residing within the proximal bone contacting portion 20. In this manner, longitudinally expanding the expandable distal cancellous bone contacting portion 40 will increase the amount of surface area contact between the expandable distal cancellous bone contacting portion 40 and the cancellous inner portion 4.

The expandable distal cancellous bone contacting portion 40 may also include one or more perforations or holes (not shown) to facilitate expansion and/or to permit bone cement to engage the cancellous inner portion 4 of the bone B.

The hybrid bone fixation element may be made from any biocompatible material including, but not limited to, metals such as, for example, titanium, titanium alloys, stainless steel, etc., polymers such as, for example, PEEK, PCU, etc., and combinations thereof.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A hybrid bone fixation element for engaging a patient's bone including a cortical outer portion surrounding an inner cancellous portion; the hybrid bone fixation element comprising:
a threaded proximal cortical bone contacting portion for threadably engaging the cortical outer portion of a patient's bone, the threaded proximal cortical bone contacting portion having a cannulated bore formed therein; and
a non-threaded expandable distal cancellous bone contacting portion for engaging the inner cancellous portion, the non-threaded expandable distal cancellous bone contacting portion including a plurality of closed periphery holes;
wherein the threaded proximal cortical bone contacting portion comprises an externally threaded shaft having a radial diameter, the threaded shaft coupled to the non-threaded expandable distal cancellous bone contacting portion along a longitudinal axis, the non-threaded expandable distal cancellous bone contacting portion has a first unexpanded radial diameter in a first unexpanded state substantially equal to or less than the radial diameter of the externally threaded shaft, and the non-threaded expandable distal cancellous bone contacting portion has a second expanded radial diameter in a second expanded state at least twice the radial diameter of the externally threaded shaft; and
an elongated head portion integral with the externally threaded shaft along the longitudinal axis, the head portion comprising a drive surface.

2. The hybrid bone fixation element of claim 1, wherein the closed periphery holes are formed by intersecting helices.

3. The hybrid bone fixation element of claim 2, wherein the intersecting helices are attached at intersections.

4. The hybrid bone fixation element of claim 3, wherein the intersections are integrally formed by perforations.

5. The hybrid bone fixation element of claim 4, wherein the expandable distal cancellous bone contacting portion is an expandable stent coupled to the threaded proximal cortical bone contacting portion.

6. The hybrid bone fixation element of claim 5, wherein the expandable stent is configured for expansion from a first insertion configuration to a second expanded configuration via a balloon-catheter inserted into the expandable stent.

7. The hybrid bone fixation element of claim 6, wherein the first insertion position has a first surface area and the second expanded configuration has a second surface area, the second surface area being larger than the first surface area.

8. The hybrid bone fixation element of claim 6, wherein the first insertion position has a first radial diameter and the second expanded configuration has a second radial diameter, the second radial diameter being larger than the first radial diameter.

9. The hybrid bone fixation element of claim 1, wherein the closed periphery holes are formed by at least one of holes or perforations extending through a wall of the expandable distal cancellous bone contacting portion.

10. A hybrid bone fixation element for engaging a bone having a longitudinal axis comprising:
an enlarged head having a drive surface;
at least one externally threaded shaft portion having a diameter, a proximal end and a distal end; and
an expandable stent coupled to the externally threaded shaft portion, the expandable stent having a first unexpanded diameter substantially equal to or less than the diameter of the externally threaded shaft, and a second expanded diameter at least twice the diameter of the externally threaded shaft;
wherein the expandable stent includes a plurality of closed periphery holes; and
wherein the expandable stent is coupled to the distal end of the externally threaded shaft portion and the enlarged head is coupled to the proximal end of the externally threaded shaft portion,
wherein the externally threaded shaft comprises a cannulated bore formed therein.

11. The hybrid bone fixation element of claim 10, wherein the externally threaded shaft comprises a substantially continuous outer surface having a screw thread formed thereon.

12. The hybrid bone fixation device of claim 10, wherein the stent portion in its expandable state increases in size along the longitudinal axis of the device.

13. The hybrid bone fixation element of claim 10, wherein the closed periphery holes are formed by a plurality of at least one of holes or perforations extending through a wall of the expandable distal cancellous bone contacting portion.

14. The hybrid bone fixation element of claim 10, wherein the expandable stent includes intersecting helices.

15. A hybrid bone fixation device for engaging bone having a longitudinal axis comprising:
- an enlarged head having a proximal end, a distal end and a drive surface, the enlarged head having a bore formed therethrough from the proximal end to the distal end;
- a shaft having a proximal end, a distal end and a continuous outer surface between the proximal and distal ends defining a cross-section, the outer surface having an external thread, the proximal end of the shaft coupled integrally as a monolith with the distal end of the enlarged head along the longitudinal axis, the shaft having a cannulation formed thereon in communication with the bore of the head and extending from the proximal end to the distal end of the shaft; and
- an expandable stent having a proximal end, a distal end and a first cross-section in the unexpanded state that is substantially equal to the cross-section of the shaft and an expanded state having a second cross-section that is different than the first cross-section, the proximal end of the expandable stent coupled to the distal end of the shaft along the longitudinal axis;
- wherein the expandable stent includes a plurality of closed periphery holes.

16. The hybrid bone fixation device of claim 15, wherein the expandable stent includes intersecting helices with opposite orientation and wherein the holes are defined between the helices.

\* \* \* \* \*